United States Patent
Marmier et al.

(10) Patent No.: US 9,347,865 B2
(45) Date of Patent: *May 24, 2016

(54) INSTRUMENT FOR GRAVIMETRIC MOISTURE DETERMINATION WITH ELECTRICAL CONTACT

(71) Applicant: Mettler-Toledo AG, Greifensee (CH)

(72) Inventors: Yves Marmier, La Chaux-de-Fonds (CH); Beat Albrecht, Zürich (CH); Beat Meister, Nänikon (CH)

(73) Assignee: METTLER-TOLEDO GMBH, Greifensee (CH)

( * ) Notice: Subject to any disclaimer, the term of this patent is extended or adjusted under 35 U.S.C. 154(b) by 533 days.

This patent is subject to a terminal disclaimer.

(21) Appl. No.: 13/631,624

(22) Filed: Sep. 28, 2012

(65) Prior Publication Data
US 2013/0081455 A1 Apr. 4, 2013

(30) Foreign Application Priority Data

Sep. 30, 2011 (EP) .................................... 11183599

(51) Int. Cl.
| | |
|---|---|
| G01N 5/04 | (2006.01) |
| G01N 5/02 | (2006.01) |
| G01N 5/00 | (2006.01) |

(52) U.S. Cl.
CPC .................. *G01N 5/045* (2013.01); *G01N 5/00* (2013.01); *G01N 5/02* (2013.01); *G01N 5/025* (2013.01); *G01N 5/04* (2013.01)

(58) Field of Classification Search
CPC ......... G01N 5/045; G01N 5/025; G01N 5/04; G01N 5/02; G01N 5/00
USPC .................................................. 73/73, 76, 75
See application file for complete search history.

(56) References Cited

U.S. PATENT DOCUMENTS

| | | | |
|---|---|---|---|
| 2,102,972 A | 12/1937 | Phillips | |
| 2,392,077 A * | 1/1946 | Wilson | .......................... 219/431 |

(Continued)

FOREIGN PATENT DOCUMENTS

| | | | |
|---|---|---|---|
| CN | 201312728 Y | * | 9/2009 |
| DE | 937268 | | 12/1955 |

(Continued)

*Primary Examiner* — Hezron E Williams
*Assistant Examiner* — Marrit Eyassu
(74) *Attorney, Agent, or Firm* — Standley Law Group LLP (57) ABSTRACT

An instrument (10) for gravimetric moisture determination has a housing (20) and a weighing device (40) arranged inside. The weighing device has a load receiver (60) onto which a sample (62) is placed. The housing has stationary (21) and movable (22) housing parts, the movable housing part alternately occupying a measuring and a loading position. wherein in the loading position the stationary housing part and the movable housing part are spaced apart from each other in such a way that a the sample can be put on the load receiver, wherein in the measuring position the respective housing parts form an essentially enclosed testing compartment (30) surrounding the load receiver (60), and wherein a sample-heating means (70) is arranged in the testing compartment to heat the sample on the load receiver. The instrument also has an electrical contact means (85) with first (86) and second parts (87). The first part is connected to the movable housing part and the second part is connected to the stationary housing part. In the measuring position an electrical connection exists by way of the respective parts of the electrical contact means and wherein in the loading position the same electrical connection is interrupted.

18 Claims, 8 Drawing Sheets

(56) References Cited

U.S. PATENT DOCUMENTS

| | | |
|---|---|---|
| 5,485,684 A | 1/1996 | Philipp et al. |
| 5,617,648 A | 4/1997 | Leisinger et al. |
| 5,787,600 A | 8/1998 | Leisinger et al. |
| 6,255,603 B1 | 7/2001 | Spannagel et al. |
| 6,463,714 B2 | 10/2002 | Viaud |
| 7,000,527 B2 * | 2/2006 | Payen .................... A47J 36/38 55/467.1 |
| 7,617,717 B2 | 11/2009 | Lüchinger |
| 7,851,712 B2 | 12/2010 | Lüchinger |
| 2001/0039831 A1 * | 11/2001 | Olesen ............................... 73/73 |
| 2003/0060071 A1 * | 3/2003 | Passow et al. ................ 439/188 |
| 2006/0021803 A1 | 2/2006 | Iiduka et al. |
| 2007/0245813 A1 * | 10/2007 | Luchinger ......................... 73/76 |
| 2007/0256479 A1 * | 11/2007 | Luchinger ......................... 73/76 |

FOREIGN PATENT DOCUMENTS

| | | |
|---|---|---|
| DE | G8802378.8 U1 | 4/1988 |
| DE | 4134818 A1 | 4/1993 |
| FR | 2606510 A1 | 5/1988 |
| WO | 2010/012391 A1 | 4/2010 |

\* cited by examiner

INSTRUMENT FOR GRAVIMETRIC MOISTURE DETERMINATION WITH ELECTRICAL CONTACT

CROSS-REFERENCE TO RELATED APPLICATIONS

This application is entitled to benefit of a right of priority under 35 USC §119 from European patent application 11183599.7, filed 30 Sep. 2011, the content of which is incorporated by reference as if fully recited herein.

TECHNICAL FIELD

The present invention relates to a measuring instrument for the gravimetric determination of moisture content.

BACKGROUND

The moisture content of a sample is determined by drying the sample and by manually determining its weight before and after the drying process. Due to the laborious procedures involved, this method is very expensive and error-prone.

Under certain conditions, the weight loss can also be determined during the drying process. For a given sample, the measured value for the weight decreases as a function of the temperature, the elapsed drying time, and the parameters of the testing compartment, according to a weight vs. time profile graph which asymptotically approaches the dry weight of the sample. The graph for the sample under examination can be determined through comparison experiments and expressed mathematically in the form of an approximation formula. Based on the available electronic capabilities, an appropriately equipped measurement instrument for the gravimetric determination of moisture content is able to calculate the moisture content of a sample from the measured parameters of the profile graph and the drying time and to indicate the moisture content on a display unit. With this method, it is no longer necessary for the material under test to be completely dried out, because sufficient information is obtained by determining the coordinates of two measurement points in the weight/time diagram.

As mentioned above, the change in the weight of a sample is essentially a function of the temperature, the elapsed drying time, and the parameters of the testing compartment. The instruments that are commercially available at this time are limited in their accuracy primarily because of the demanding requirements which have to be met by the testing compartment.

Normally, the sample is spread in a thin layer onto a flat sample receiver, for example a sample tray. The tray is arranged inside the gravimetric moisture determination instrument with the sample-receiving surface extending horizontally and parallel to the heat-emitting surface of the sample-heating means, in order to achieve a uniform heating of the sample.

Devices that are used as sample-heating means include a variety of radiation sources such as radiant heaters, microwave generators, halogen- and quartz lamps. As could be established by experiments, one of the main causes for the inaccuracy in the determination of measurement values in existing gravimetric moisture-determination instruments lies in the nature of the radiation sources being used and in their arrangement in the testing compartment.

A measuring instrument of the aforementioned kind for the gravimetric determination of moisture content is described in the European Patent EP 0 611 956 B1. In this instrument, the loading of the weighing pan occurs outside of the gravimetric moisture-determination instrument. To load and unload the sample, the balance which is arranged on a drawer-like carriage is slid out of the instrument housing. As a radiation source, a ring-shaped halogen lamp is being used which, in the operating state of the apparatus, is arranged above the sample receiver. Examples of further design configurations are published in EP 1850 110 A1. For example, a measuring instrument is disclosed which is opened up for loading through a horizontal swivel movement of a part of the housing. In a further embodiment, a part of the housing is swiveled in the vertical direction. Likewise, the measuring instruments disclosed in U.S. Pat. No. 7,851,712 B2 are opened for loading by vertically swiveling a part of the housing.

All of these types of designs have the disadvantage that their radiation sources, hereinafter also referred to as sample-heating means, can be hot and therefore pose a risk of injury to the user. Furthermore, a technician servicing the equipment can be exposed to the danger of an electric shock.

It is therefore the object of the present invention to provide a measuring instrument for gravimetric moisture determination which offers the assurance of user safety.

SUMMARY

This task is solved by the measuring instrument of the present invention for gravimetric moisture determination in accordance with claim 1 and its dependent claims.

The measuring instrument of the present invention for gravimetric moisture determination comprises a housing and a weighing device arranged inside the housing. The weighing device has a load receiver onto which a sample can be placed. The housing has a stationary housing part and a movable housing part, wherein the movable housing part can occupy positions for measuring and for loading, respectively. In the loading position, the stationary housing part and the movable housing part are spaced apart from each other in such a way that a sample can be put on the load receiver. Normally, the sample is manually placed on the load receiver. In the measuring position, the stationary housing part and the movable housing part form an essentially closed-up testing compartment around the load receiver. For the heating of a sample that is placed on the load receiver, there is a sample-heating means arranged in the testing compartment. The sample-heating means is converting electrical energy into heat. According to the invention, the measuring instrument includes an electrical contact means with a first part and a second part. The first part of the electrical contact means is connected to the stationary housing part, and the second part of the electrical contact means is connected to the movable housing part. In the measurement position, an electrical connection exists by way of the first and the second part of the electrical contact means. In the loading position, the electrical connection between the first and the second part of the electrical contact means is interrupted.

The term "housing part" in the present context is meant to include the elements of the instrument that are attached to it. Typically, the sample-heating means is arranged on the movable housing part while the weighing device, the sample receiver and the electronic module are arranged on the stationary housing part.

The term "testing compartment" means a space which is enclosed by the housing of the measuring instrument and which can be opened and closed in order to bring in or take out a sample. Arranged inside the testing compartment are a sample receiver and a means for heating the sample. The sample receiver is connected to a gravimetric measuring instrument. The gravimetric measuring instrument can also be referred to as a weighing device.

Ideally, only the stationary housing part is connected to the electric grid, while the movable part is supplied with electricity only through the electrical contact means. This arrangement serves to ensure that the movable housing part receives electricity only while the instrument is in measuring position. In the loading position, there is no current flowing to the movable housing part. Consequently, as the sample-heating means is not supplied with current during loading and servicing, the sample-heating means cannot heat up during loading and the danger of burn injuries to the user is reduced.

Preferably, the first part of the electrical contact means has an essentially rigid connection to the stationary housing part, and the second part of the electrical contact means has an essentially rigid connection to the movable housing part. Possible choices for the electrical contact means include for example suitably configured plug and socket connections.

In a preferred embodiment, the movable housing part and the stationary housing part are not connected by any additional electronic contact means through which for example control signals could be sent from the stationary housing part to the movable housing part. In the movable housing part there are no components that require or emit control signals. The sample-heating means is controlled exclusively by the supply current which flows through the first and second contact means. Accordingly, the temperature of the sample-heating means is controlled only through the power supply.

In a preferred embodiment of the invention, the movable housing part can be brought by means of a position-shifting device in a translatory movement from the measuring position into the loading position. As a result of this movement, the electrical contact between the first and the second part of the electrical contact means is interrupted. If in addition to the electrical contact means, there are electronic contact means provided, their connection would likewise be interrupted.

The electrical contact means are advantageously configured as a plug-in connection, i.e. a connection between a plug and a socket. The insertion of the plug into the socket should occur in an essentially vertical direction. A pivotable, concentric plug connection of the kind used in water heaters has proven particularly suitable as electrical contact means. The pivotable, concentric plug connection is particularly robust and reliable in closing and opening an electrical contact.

Preferably, the movable housing part is movable in the horizontal and in the vertical direction. It is particularly advantageous if the movement takes place simultaneously in a horizontal and a vertical direction. The movement, more specifically the translatory displacement, of the movable housing part can take place as a parallel displacement. This displacement shifts the movable housing part simultaneously in the upward direction and to the rear, i.e. away from the user. When the movable housing part is moved from the loading position to the measuring position, the movement has the result of connecting the electrical contact means to each other.

In a preferred embodiment, the movable housing part is located above the stationary housing part, both in the measurement position and in the loading position of the apparatus. This can be realized with a configuration where the movable housing part is significantly shorter than the stationary housing part in the direction of horizontal movement. Ideally, the length of the movable housing part is less than half the length of the stationary housing part. The position-changing means is designed so that when the movable housing part is moved, it is always at a location above the stationary housing part.

Ideally, the heating means is arranged in the movable housing part in such a way that in the measuring position the sample-heating means is located above the sample receiver, and in the loading position the sample-heating means is located above the stationary housing part. This has the advantage that the sample can be heated from above. As the sample-heating means is arranged on top, it is less susceptible to collecting dirt.

The heating means is designed so that it can be swiveled together with the movable housing part from the measuring position into the loading position. This has the essential advantage that it reduces the danger of injury, because neither in the measuring position nor in the loading position can the heating means be inadvertently touched by the user.

Ideally, the heating means in the measurement position and/or loading position is arranged so that its surface spreads in essence horizontally over the sample receiver and between the stationary housing part and the movable housing part.

For the purpose of servicing, at least a portion of the movable housing part can be pivoted from the loading position into a servicing position about an essentially horizontal tilt axis. The tiltable portion of the movable housing part contains the heating means which, in the servicing position, is thus made accessible for a service technician for the purpose of servicing. In the servicing position, there is likewise no electric current flowing to the movable housing part. Thus, neither the user nor the service technician is exposed to the danger of an electric shock.

According to the invention, the sample-heating means is arranged in the movable housing part and, in the servicing position, removable without tools. Advantageously, when the movable housing part is in the servicing position, a service opening provides access to allow the sample-heating means to be removed. Also, in the servicing position, the sample-heating means is in essence oriented in a vertical position. Thus, the sample-heating means is facing the user and more easily accessible.

BRIEF DESCRIPTION OF THE DRAWINGS

Details of the measuring instrument according to the invention may be learned from the description of the embodiment illustrated in the drawings, wherein FIG. 1 in a sectional view, shows a schematic representation of a measuring instrument according to the invention in measuring position.

DETAILED DESCRIPTION OF THE DRAWINGS

Figure 1:
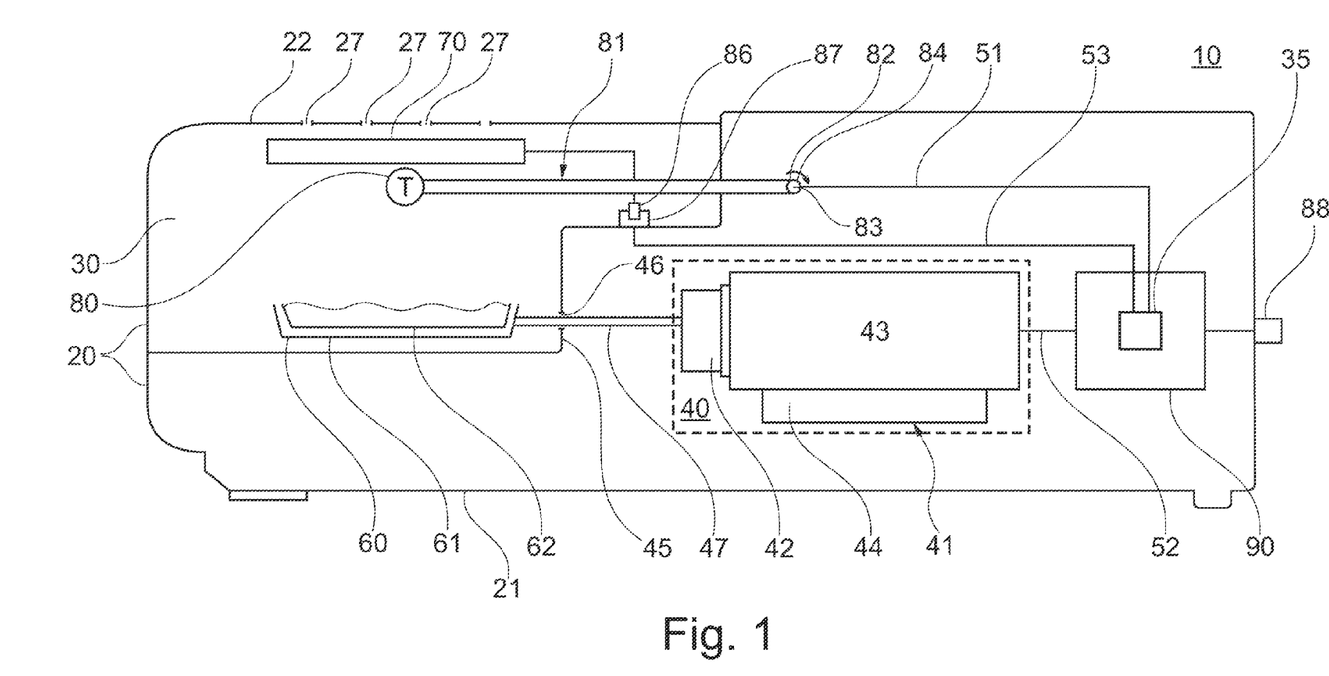
Figure 2:
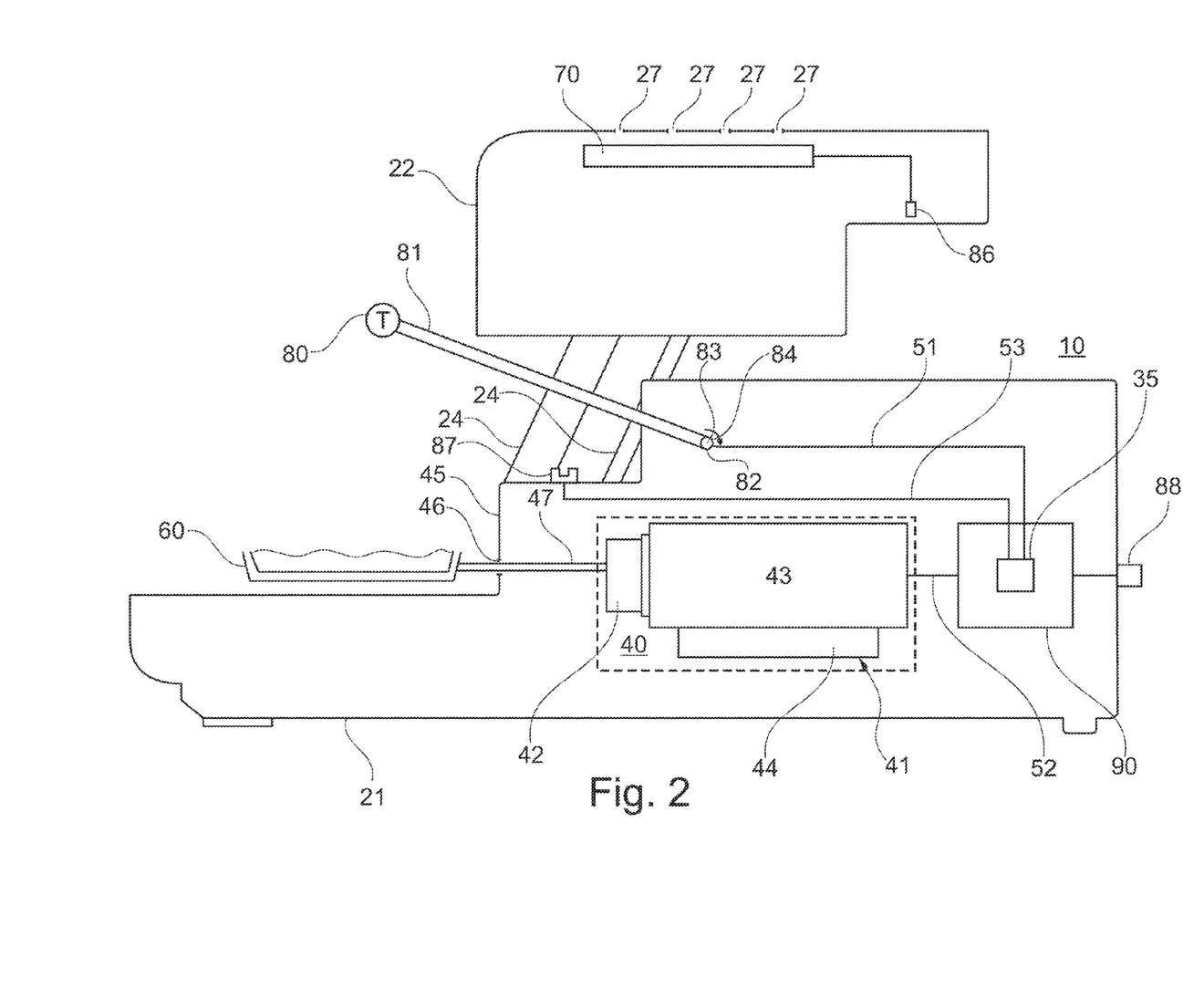
FIG. 2 in a sectional view, shows a schematic representation of the measuring instrument of FIG. 1 in loading position.

FIGS. 1 and 2 represent schematic, sectional views of a measuring instrument 10 according to the invention in measuring position (FIG. 1) and in loading position (FIG. 2). The measuring instrument 10 has a housing 20 in which a testing compartment 30 is arranged. The housing 20 is subdivided into a movable housing part 22 and a stationary housing part 21. When the instrument is in use, the stationary housing part 21 is standing on a solid support surface. The movable housing part 22 is attached to the stationary housing part. To the rear, i.e. on the side of the testing compartment 30 that faces away from the user, a weighing device 40 is arranged in the stationary housing part 21. The movable housing part 22 is constrained on the stationary housing part 21 by means of a translatory-motion guide 24. The translatory-motion guide 24 is configured so that the movable housing part 22 maintains an essentially constant orientation during its movement from the measuring position into the loading position. In other words, during its movement the movable housing part 22 remains essentially parallel to the stationary housing part 21. The stationary housing part 21, which is configured as a hollow body, contains a weighing cell 43 and at least one electronic module 90 which are connected to each other by transfer means 52. The electronic module 90 includes at least one signal-processing module (not shown in detail) and in some cases also a controller- and/or regulator module. The weighing cell 43 has at least one stationary portion 41 and a load-receiving portion 42. State-of-the-art types of weighing cells include for example elastic deformation bodies carrying strain gauges, weighing cells that operate according to the principle of electromagnetic force compensation, weighing cells with oscillating strings, capacitative weighing sensors and the like. The stationary portion 41 is solidly connected to the stationary housing part 21. Arranged on the load-receiving portion 42 is a connecting member 47 through which a sample receiver 60 is connected to the load receiving portion 42 of the weighing cell 43. As shown in the drawing, a sample tray 61 with a sample 62 can be set on the sample receiver 60. If the sample receiver 60 is suitably configured, the sample 62 can of course also be put directly on the sample receiver 60.

The measuring instrument 10 as shown in FIG. 1 is in measuring position which means that the sample receiver 60 and the sample receiver 61 sitting on it are inside the testing compartment 30. The stationary housing part 21 and the movable housing part 22 form an essentially enclosed testing compartment 30 surrounding the sample receiver 60. A heating means 70 is arranged essentially parallel to the plane of the sample receiver 60, so as to obtain as homogeneous a heat distribution as possible at least on the surface of the sample 62. It is also possible to arrange an additional heating means in the testing compartment 30 below the sample receiver 60 in order to expose the underside of the sample 62 to radiation. However, it is not absolutely necessary to arrange the heating means 70 parallel to the plane of the sample receiver 60. Depending on the sample 62 and on the measurement that is to be performed, it may also be advantageous to arrange the heating means 70 at an oblique angle to the sample receiver 60.

To allow the moisture given off by the sample 62 to escape from the testing department 30, the housing 20 has outlet vents 27 arranged at an appropriate location of in the movable housing part 22, preferably above the heating means 70. To generate sufficient air circulation inside the testing compartment 30, there should further be air vent openings provided at appropriate locations.

The measuring instrument 10 in FIG. 1 is shown in measuring position. The stationary housing part 21 and the movable housing part 22 form an essentially enclosed testing compartment 30. The latter is essentially delimited at the top by the movable housing part 22 and at the bottom by the stationary housing part 21. The heating means 70 is arranged in the movable housing part 22. Ideally, the heating means 70 is mechanically connected to the movable housing part 22 through releasable plug-in connections. Thus, the heating means 70 can be uninstalled without much effort for cleaning or repair. Furthermore, with the use of plug-in connections the user of the measuring instrument 10 is able to select from different heating means with different functional characteristics. This enables the user to match the conditions inside the testing chamber to a specific sample 62.

The measuring instrument 10 includes an electronic module 90 which is arranged in the stationary housing part 21. The electronic module 90 has a variety of controller/regulator devices. Among others, the electronic module 90 also includes a controller/regulator device for the control and regulation of the heating means 70. A temperature sensor 80 which is illustrated schematically in the drawing serves to measure the temperature of the sample 62 and to deliver to the controller/regulator device 35 the information required for the regulation of the heating means 70. The controller/regulator device 35 is further connected to the weighing device 40, specifically to the electronic module 90, by means of at least one transfer means 52. The transfer means 52 serves for the transmission of electrical and/or electronic signals. As a result, the controller/regulator device 35 can be accessed by means of the electronic module 90. The measuring instrument 10 is supplied with power by means of an electrical connection 88. The electrical power connection 88 is arranged on the stationary housing part 21. Preferably, the electrical current is delivered only by way of the stationary housing part 21. Thus, the user or the service technician is not subjected to the risk of receiving an electric shock in the course of a servicing operation.

The controller/regulator device 35 and the temperature sensor 80 are connected to each other through a transfer means 51. Furthermore, the controller/regulator device 35 and the sample-heating means 70 are connected to each other through a further transfer means 53. The transfer means 51, 53 serve to transmit electrical and electronic signals between the respective apparatus components. During the measurement process, the temperature in the testing compartment 30 is measured by means of the temperature sensor 80. The temperature signal generated by means of the temperature sensor 80 is transmitted by way of the transfer means 51 to the controller/regulator device 35. For the controller/regulator device 35 the temperature signal is an input signal based on which the sample-heating means 70 is controlled. In the measurement position, the temperature sensor 80 is located between the sample receiver 60 and the sample-heating means 70. This arrangement makes it possible to obtain the temperature value that is relevant for the measurement. The temperature sensor could also be placed at a different location. However, the temperature values that are thereby obtained are less accurate in representing the heat level in the testing compartment. The temperature sensor 80 is arranged on a rod 81 which is fastened to the stationary housing part 21. The rod 81 is essentially rigid, with a first end and a second end. Arranged at the first end is the temperature sensor 80, while the second end is connected to the stationary housing part 21. Due to the fact that the second end is connected to the stationary housing part 21, the operation of the temperature sensor 80 does not require an electrical and/or electronic connection from the stationary housing part 21 to the movable housing part 22.

The transfer means 51 is arranged at or inside the rod 81. The rod 81 can be swivel on a fulcrum pivot 82. The fulcrum pivot 82 is at the second end of the rod 81 and has a substantially horizontal pivot axis 83.

The rod 81 and the fulcrum pivot 83 are arranged so that during the change from the measuring position to the loading position, the temperature sensor 80 moves along a circular path in a vertical plane. Arrangements are also possible where the circular path lies in a different, i.e. non-vertical plane. For example, the axis of the fulcrum pivot can be given an essentially vertical orientation, so that the temperature sensor 80 is constrained to a circular path in a horizontal plane during the change from the measuring position to the loading position.

In the measuring position, the rod 81 is force-biased by the spring tension of a spring element 84. When the movable housing part 22 is brought from the measuring position into the loading position, the rod 81 is moved away from the sample receiver 60 by the elastic force of the pre-tensioned spring element 84. In the loading position, the temperature sensor 80 and the rod 81 are therefore not obstructing the access to the sample receiver 60, which facilitates the loading of the measuring instrument. Ideally, the spring element 84 is constituted by a torsion spring wherein the torque axis coincides with the axis of the fulcrum pivot 83. Of course, other spring elements could also be used, such as for example compression spring elements. In any case, the spring element needs to be arranged so that it is elastically biased in the measuring position while being unstressed or less biased in the loading position.

As the sample-heating means 70 is arranged in the movable housing part 22 and the controller- and regulator device 35 is arranged in the stationary housing part 21, the transfer means 53 has to transmit electrical and/or electronic signals from the stationary housing part 22 to the movable housing part 21. This can be accomplished for example with a flexible cable. However, due to the position shifts of the movable housing part 21, this cable would be subjected to bending cycles and therefore susceptible to wear.

This problem can be circumvented by using an electrical contact means with a first part 86 and a second part 87, wherein the first part 86 is connected to the movable housing part 22 and the second part 87 is connected to the stationary housing part 21. Under this concept, the first and the second part of the electrical contact means 86, 87 are arranged so that in the measuring position the first and second part 86, 87 form an electrical connection, and that in the loading position the electrical connection is interrupted. It is a significant advantage of this arrangement that in the loading position the sample-heating means 70 is not supplied with electricity. Ideally, the electronics for the control are arranged exclusively in the stationary housing part 22. The control of the sample-heating means 70 takes place only by way of the first and second electrical contact means 86, 87. Therefore, no connection is needed for the transmission of control signals to the movable housing part 21. This is a further reason for arranging the temperature sensor 80 on the stationary housing part 21. If the temperature sensor 80 were arranged on the movable housing part 22, it would be necessary to transmit signals between the stationary housing part 21 and the movable housing part 22. As a further advantage of the measuring instrument 10 according to the invention, the temperature can also be measured and registered in the loading position by means of the temperature sensor 80. Thus, it is for example possible to measure the ambient temperature during the loading process.

The electrical contact means 86, 87 include a plug-in connection where one of the two parts of the electrical contact means 86 is configured as a plug and the other part as socket that cooperates with the plug. The direction of insertion of the plug connection is essentially vertical.

In FIG. 2 the measuring instrument 10 of FIG. 1 is shown in loading position. By means of a translatory-motion guide 24, the movable housing part 22 can be moved away from the stationary housing part 21, whereby the measuring instrument 10 is brought from the measuring position into the loading position. In this change of position, the movable housing part 22 undergoes in essence a purely translatory displacement. In the loading position the movable housing part 22 is located above the stationary housing part 21 and above the weighing device 40. The sample-heating means 70 in this position is located between the movable housing part 22 and the stationary housing part 21. This prevents accidental touching of the sample-heating means 70 which may be very hot.

In the change to the loading position, the temperature sensor 80 is moved upward and laterally away from the sample receiver 60. Thus, the temperature sensor 80 will not interfere with the loading of the sample receiver 60.

In the loading position, the electrical contact means 86, 87 is interrupted. There is no electricity flowing from the stationary housing part 21 to the movable housing part 22. Since the movable housing part 22 does not have power connection of its own, no electric current is entering the movable housing part 22 in the loading position.

Figure 3A:
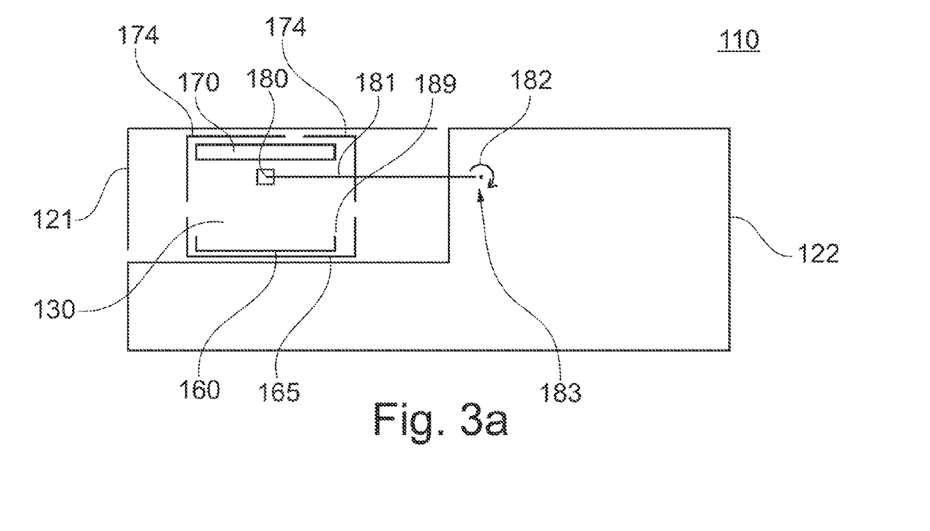
FIG. 3a shows a schematic representation of a further measuring instrument according to the invention with a temperature sensor, wherein the latter is in measuring position.
Figure 3B:
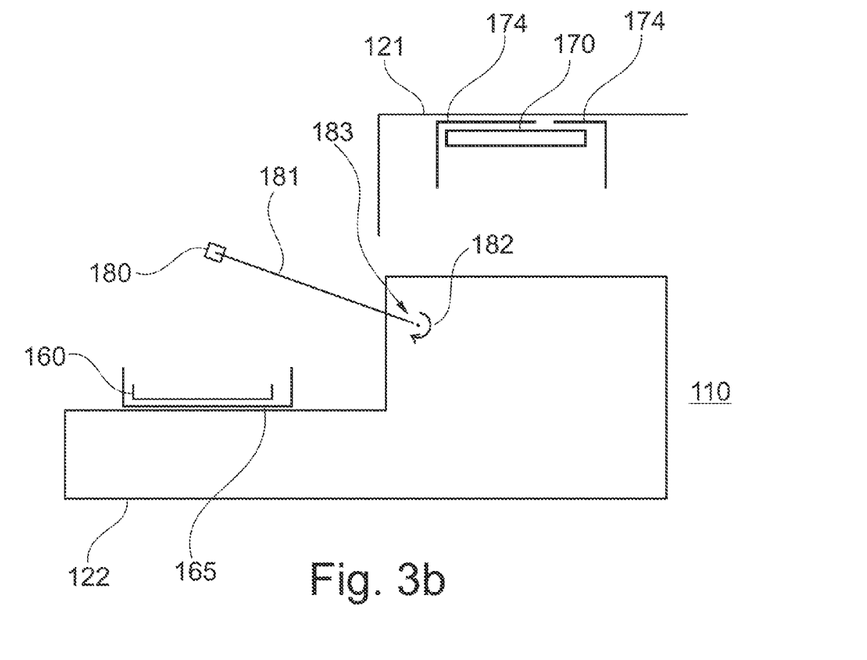
FIG. 3b shows a schematic representation of the measuring instrument of FIG. 3a, wherein the temperature sensor is in the loading position.

FIGS. 3a and 3b illustrate a further measuring instrument 110 according to the invention in a schematic representation. FIG. 3a shows the measuring instrument 110 in the measuring position, and FIG. 3b shows the same measuring instrument 110 in the loading position.

The measuring instrument 110 has a housing 120 with a stationary housing part 121 and a movable housing part 122.

When the instrument is in measuring position, the stationary housing part 121 and the movable housing part 122 together form an essentially enclosed testing compartment 130, in which the sample receiver 160 is located. Arranged above the sample receiver 160 is a sample-heating means 170. The sample-heating means 170 is solidly connected to the movable housing part 122. A temperature sensor 180 is arranged on a rod 181. The rod 181 has a first and a second end. Attached to the first end is the temperature sensor 180, while the second end is pivotally connected to the stationary housing part 121. In the measuring position of the instrument, the temperature sensor 180 is located above the load receiver 160 and underneath the sample-heating means 170. In loading position, the temperature sensor 180 is located essentially off to the side of the load receiver 160. This is accomplished with a design where the rod 181 is rigid and is connected to the stationary housing part 121 by means of a fulcrum pivot 182. Ideally, the axis 183 of the fulcrum pivot 182 is oriented horizontally. In measuring position, the rod 181 can be spring-biased by the elastic force of a spring element. When the movable part 122 is moved from the measuring position into the loading position, the rod 181 is moved upwards and laterally in a circular arc by means of the biasing force of the spring element. In measurement position, the spring element is preferably held in a pre-tensioned state by the movable housing part 122.

Figure 6:
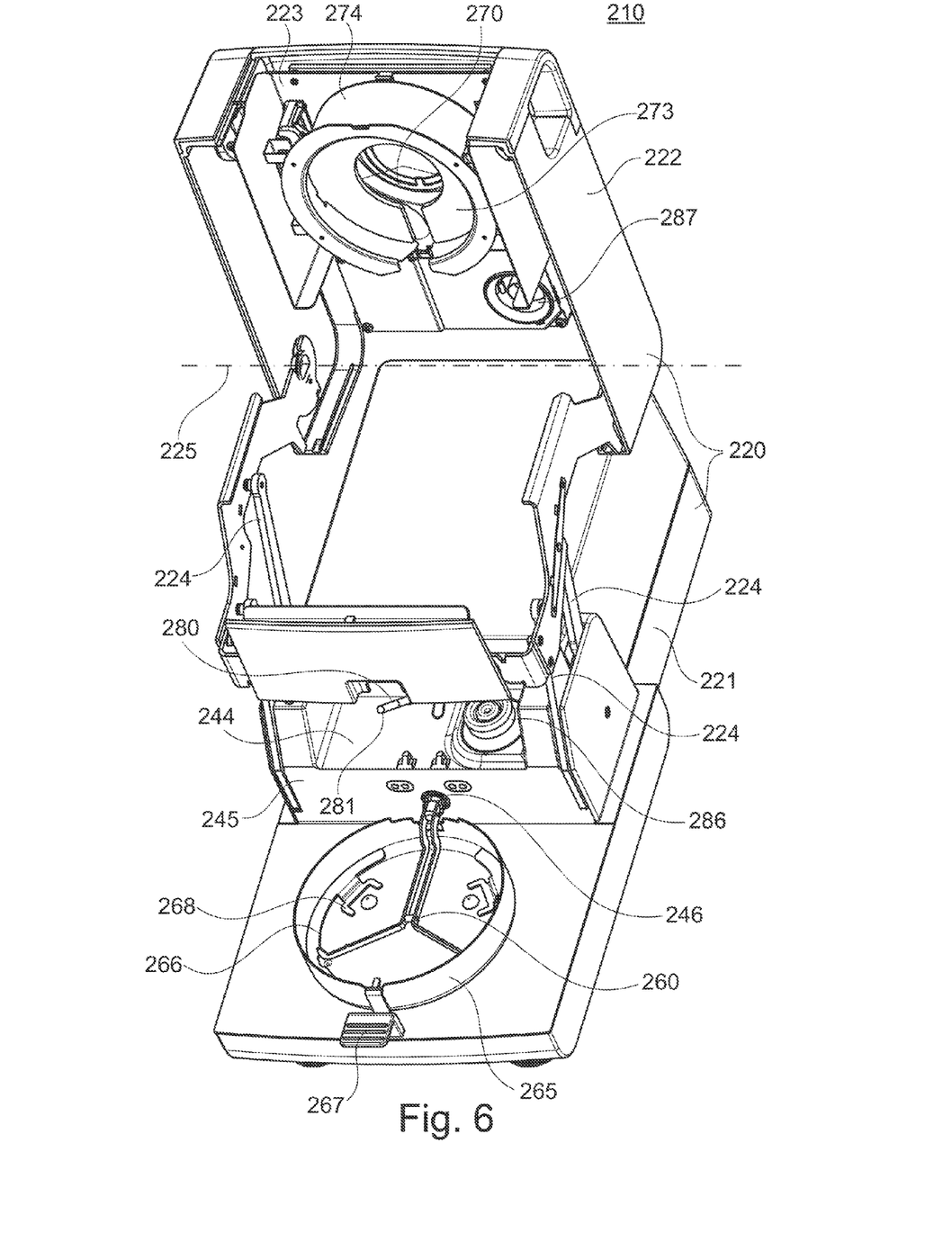
FIG. 6 shows the measuring instrument of FIG. 4 in servicing position.
Figure 7:
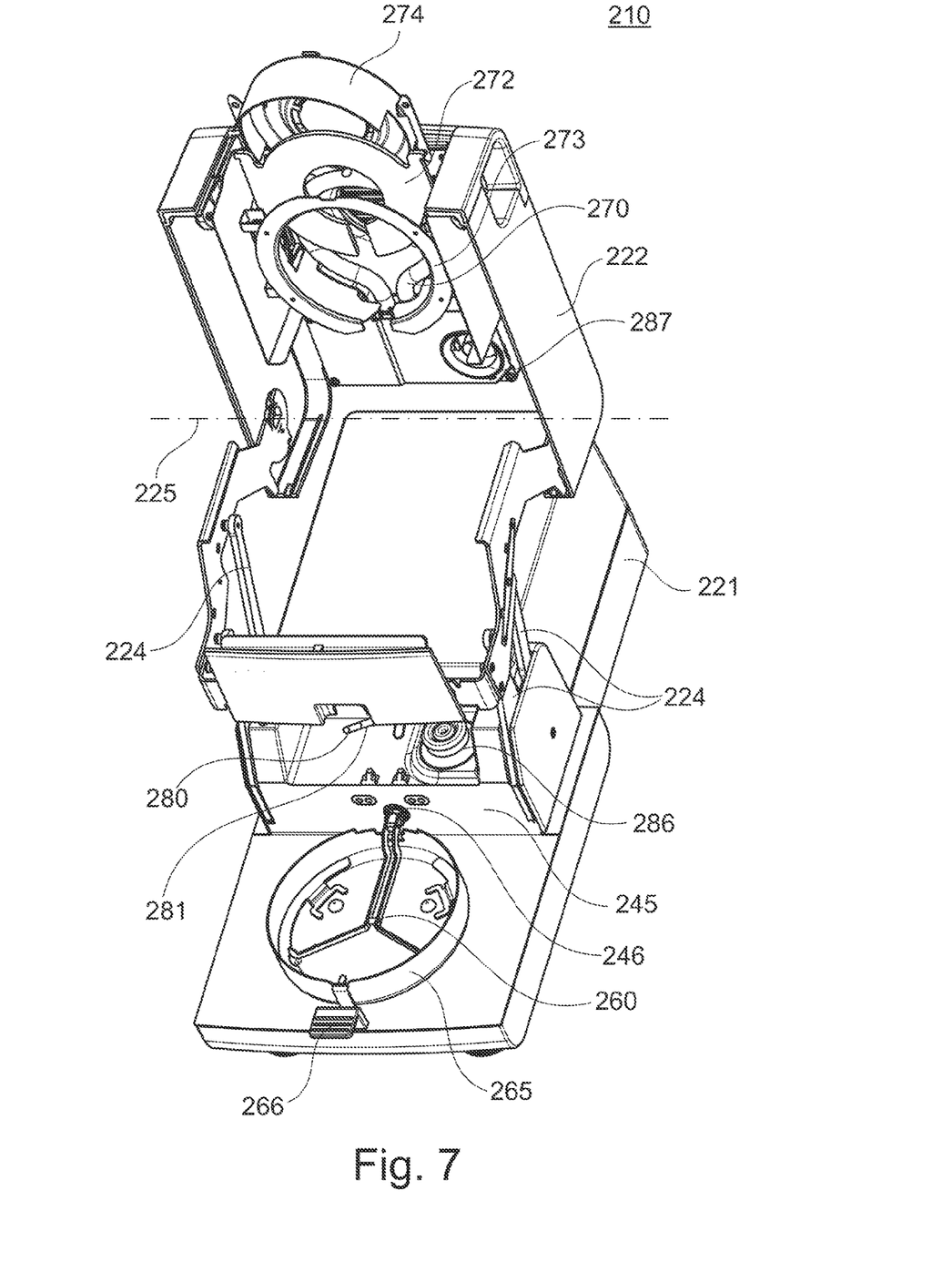
FIG. 7 shows the measuring instrument of FIG. 6 in servicing position with partially removed glass shield and draft protector.
Figure 8:
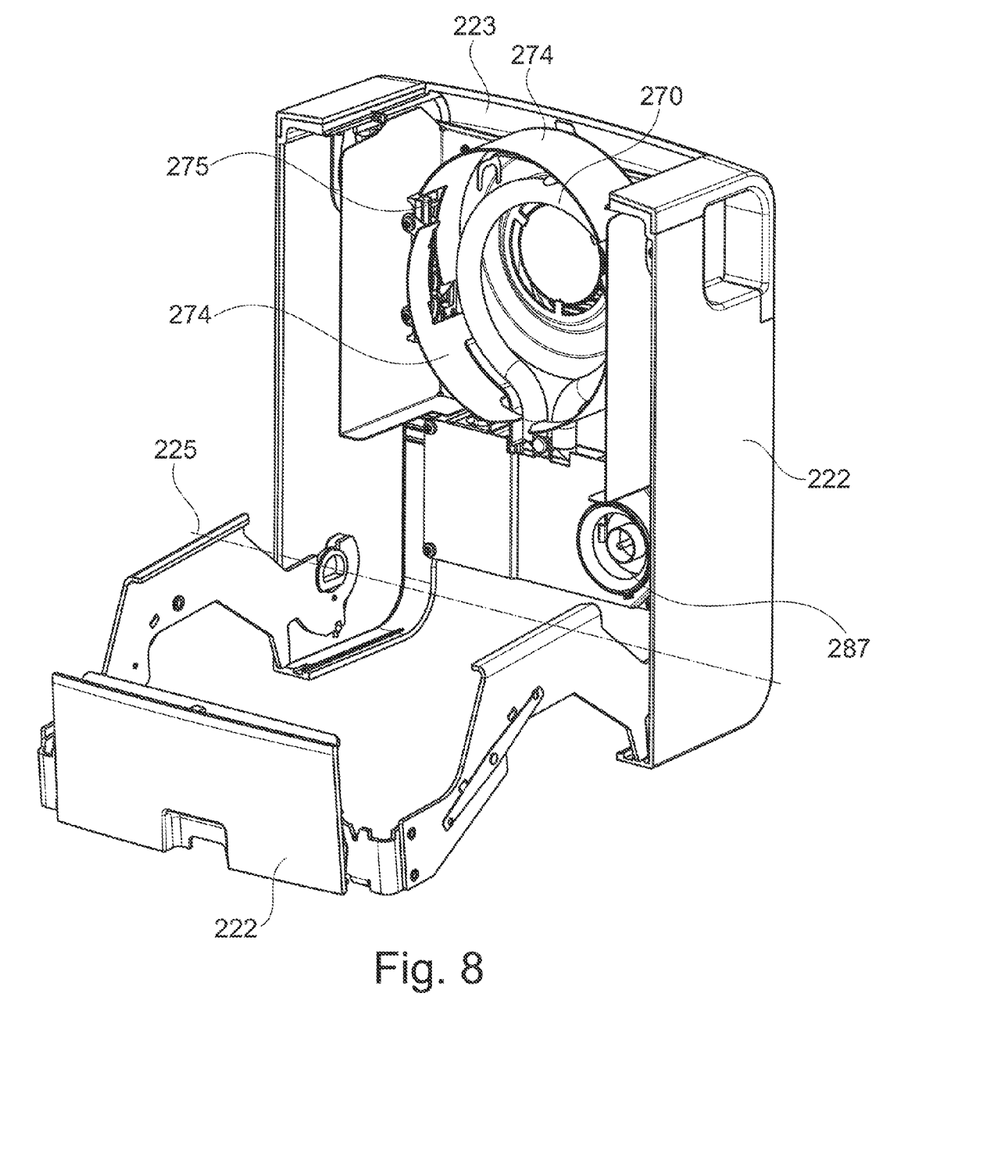
FIG. 8 shows the movable housing part of the measuring instrument of FIG. 7 in servicing position without glass shield.

To obtain the most stable measurement results possible, there can be an interior draft shield arranged inside the testing compartment (see FIGS. 6-8). This interior draft shield is arranged so that it surrounds the sample receiver 160 and the sample-heating means 170, delimiting a nearly enclosed section of space. The interior draft shield can include an upper part 174 and a lower part 165. The upper part 174 is arranged on the movable housing part 122. The upper part 174 of the interior draft shield forms a cylindrical interior space which is open towards the sample receiver. Arranged inside this cylindrical interior space is the sample-heating means. The upper part of the interior draft shield can consist of a cylindrical circumference wall alone. However, it is advantageous if the cylinder has an upper end wall which is horizontally oriented in the measuring and in the loading position of the instrument. This end wall is preferably arranged above the sample-heating means 170. Ideally, the side of the end wall that faces towards the sample-heating means 170 is heat-reflecting. Consequently, a part of the heat that is being generated is reflected by the interior draft shield and used to heat the sample which is located on the sample receiver 160. The lower part 165 of the interior draft shield is arranged on the stationary housing part 121. The lower part 165 of the interior draft shield forms a cylindrical interior space which is open towards the sample-heating means 170. Arranged in this cylindrical interior space is the sample receiver 160. In measuring position, the interior space of the upper part 174 of the interior draft shield and the interior space of the lower part 165 of the interior draft shield form an interior space in which the sample-heating means and 170 and the sample receiver 160 are located. The upper as well as the lower part of the interior draft shield 165, 174 can be made of one piece of material or assembled from several sections.

FIGS. 4, 5, 6, 7 and 8 illustrate an embodiment of the measuring instrument 210 according to the invention in different positions. The measuring instrument 210 has all of the components that have already been covered in the description of the schematic drawings of FIGS. 1 and 2.

Figure 4:
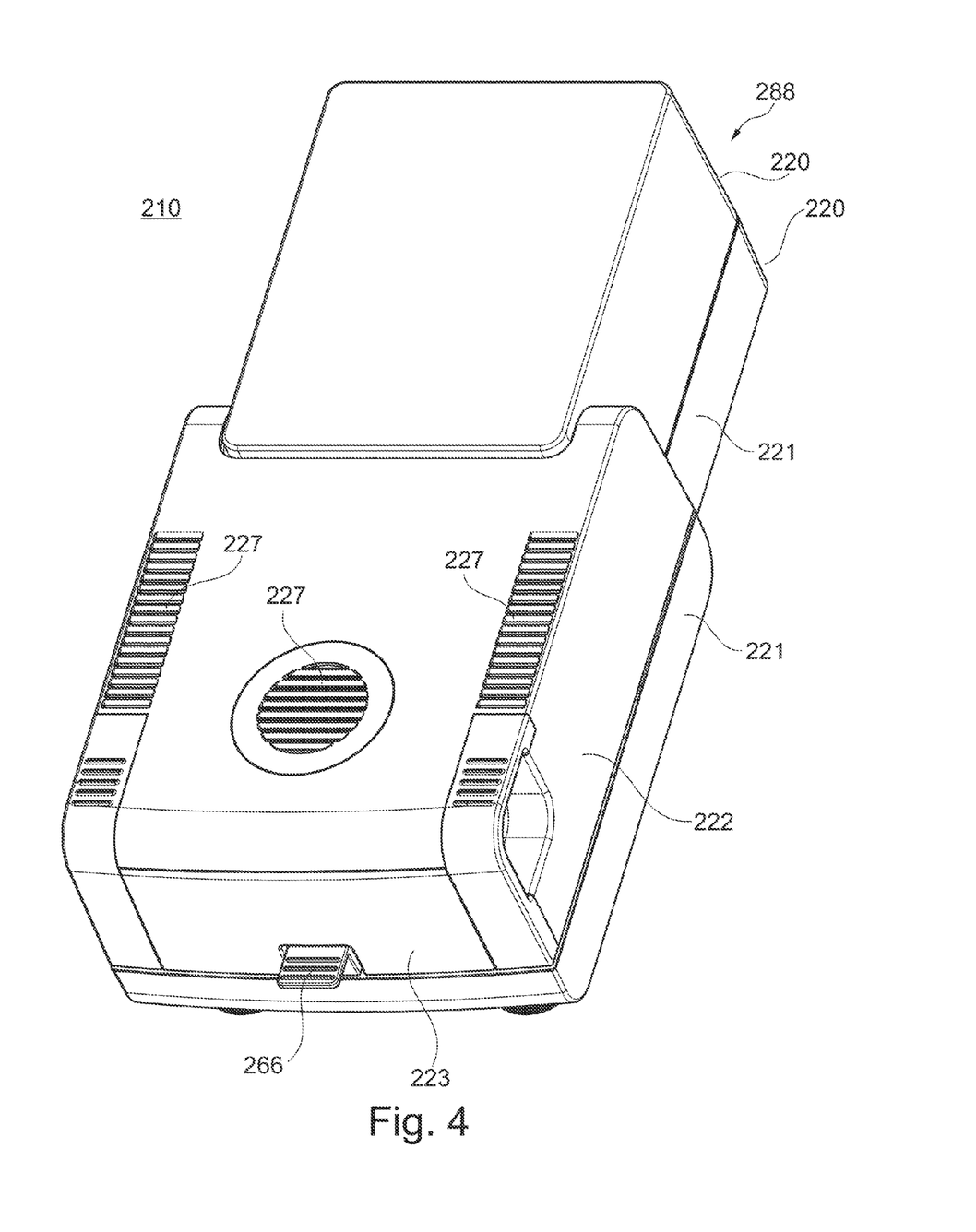
FIG. 4 shows an isometric representation of the measuring instrument according to the invention in measuring position.

FIG. 4 shows the measuring instrument 210 of the invention in measuring position. As the housing 220 is closed in the measuring position, most of the components cannot be seen. The housing 220 has a stationary housing part 221 and a movable housing part 222. In measuring position, the stationary housing part 221 and the movable housing part 222 for an essentially enclosed testing compartment. The movable housing part 222 has outlet vent openings 227 which allow gases to escape from the testing compartment inside the housing 220 into the ambient atmosphere. Advantageously, in the measurement position of the instrument the outlet vent openings 227 are located on the topside of the movable housing part 222. Especially advantageous is an arrangement of the outlet vent openings 227 above the sample-heating means 170 which is likewise arranged inside the housing 220.

Figure 5:
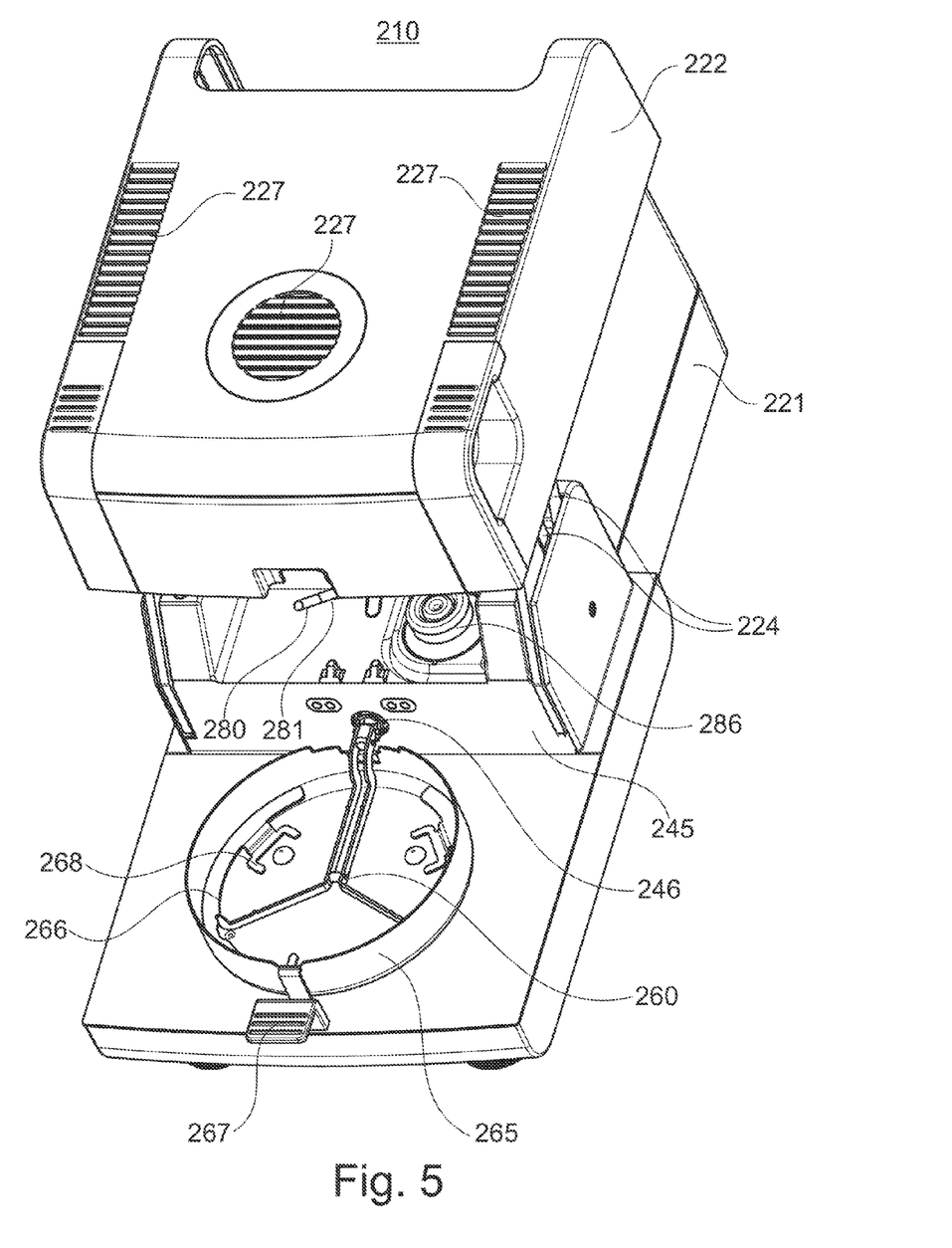
FIG. 5 shows the measuring instrument of FIG. 4 in loading position.

FIG. 5 shows the measuring instrument 210 of FIG. 4 in loading position. The movable housing part 222 has been brought from the measuring position into the loading position by a translatory movement. To enable this translatory movement, the movable housing part 222 is connected to the stationary housing part 221 by a translatory-motion guide 224. The translatory-motion guide 224 has two essentially parallel pivoting legs whose orientation defines the direction of the translatory movement of the movable housing part 222.

The stationary housing part 221 is of an elongated shape. The weighing device is largely enclosed by the stationary housing part 221. Only a sample receiver 260 which is connected to the weighing device protrudes laterally from the stationary housing part 221. Containers of various shapes such as sample trays, crucibles and the like can be put on the sample receiver 260. The stationary housing part 221 includes a portion that is located on the side of the sample receiver 260 that faces away from the user. Advantageously, in this portion the weighing device is arranged. In loading position, the movable housing part 222 is located above the stationary housing part 221, ideally above the portion that is located to the side of the sample receiver 260.

The movable temperature sensor 280 is arranged on a pivotally mounted rod 281. As described in the schematic representation of FIGS. 3a and 3b, the rod 281 is connected to the stationary housing part by means of a fulcrum pivot. The axis of the fulcrum pivot is likewise oriented horizontally, and the rod 281 is likewise elastically biased in the measuring position by means of a spring force. In the measuring position, the temperature sensor 280 is located between the sample-heating means 270 and the sample receiver 260. In the loading position, the temperature sensor 280 and the rod 281 are located to the side of and higher than the sample receiver 260. This makes it possible to load a sample on the measuring instrument 210 without the temperature sensor 280 standing in the way of the user.

The sample-heating means 270 is arranged in the movable housing part 222. During the measurement, the sample-heating means 270 becomes hot and thereby heats the sample which is arranged below the heating means on the sample receiver 260. An electric current is required for the heating. The stationary housing part 221 is therefore equipped with a power connector 288 which is arranged on the backside of the measuring instrument 210. The movable housing part does not have a power connection of its own. The electric current therefore has to be transmitted from the stationary housing part 221 to the movable housing part 222. This is accomplished with an electrical contact means which has a first part 286 and a second part 287. The first part 286 of the electrical contact means is connected to the movable housing part 222, while the second part of the electrical contact means is connected to the stationary housing part 221. The two parts 286, 287 of the electrical contact means are arranged so that in measuring position an electrical contact exists from one to the other and the sample-heating means 270 is supplied with electrical current. In the loading position, there is no contact through the electrical contact means 286, 287. The electrical contact is established automatically by the movement of the movable housing part 222. A pivotable, concentric plug connection of the kind used in water heaters has proven particularly suitable as electrical contact means. The pivotable, concentric plug connection is particularly robust and reliable in closing and opening an electrical contact. However, other configurations are likewise conceivable. Particularly suitable are plug/socket connections.

With this arrangement, an electrical connection exists in the measuring position by way of to the first and second part of the electrical contact means 286, 287, while the connection between the first and second part of the electrical contact means 286, 287 is interrupted in the loading position. In the loading position, the heating means is therefore not under power and the risk of injury is therefore reduced. The second part of the electrical contact means 286 is covered up in FIG. 5 by the movable housing part 222 and is therefore not visible.

To reduce air turbulence in the testing compartment, an interior draft shield 265, 274 which surrounds the sample receiver 260 can be arranged inside the testing compartment. This draft shield 265, 274 is preferably designed so that it conforms to the outside contour of the sample tray and/or the outside contour of the sample-heating means 270. As the sample trays being used are normally round, it suggests itself to us an interior draft shield 265, 274 with a round contour shape. The interior draft shield can include an upper part 274 and a lower part 265. The upper part 274 is arranged on the movable housing part 222. The upper part 274 of the interior draft shield encloses a cylindrical interior space which is open towards the sample receiver. Arranged inside this cylindrical interior space is the sample-heating means 270. The upper part of the interior draft shield can consist of a cylindrical circumference wall. It is advantageous if the cylinder also has at least a partial boundary surface above the sample receiver, preferably a cylinder end wall. This surface arranged preferably above the sample-heating means 270. Ideally, the side of the end wall that faces towards the sample-heating means 270 is heat-reflecting. Consequently, a part of the heat that is being generated is reflected by the interior draft shield and used to heat the sample which is located on the sample receiver 260. In addition, the end wall can have openings, so that gases can escape into the outside atmosphere from the testing compartment through the openings in the end wall and outlet vent openings in the housing 220. However, it is also possible that the end surface has no openings.

The lower part 265 of the interior draft shield is arranged on the stationary housing part 221. The lower part 265 of the interior draft shield forms a cylindrical interior space which is open towards the sample-heating means 270. Arranged in this cylindrical interior space is the sample receiver 260. In measuring position, the interior space of the upper part 274 of the interior draft shield and the interior space of the lower part 265 of the interior draft shield form an interior space in which the sample-heating means and 270 and the sample receiver 260 are located. The upper as well as the lower part of the interior draft shield 265, 274 can be made of one piece of material or assembled from several sections.

To set a sample tray in place in the testing compartment, it is possible to use a sample tray holder 266. The sample tray holder 266 has a handle 267 and seating surfaces 268 for the sample tray. During the transfer of the sample tray, the rim of the latter rests on the seating surfaces 268. During the measurement, the sample tray rests only on the sample receiver 260 and the sample tray holder 266 does not touch the sample tray. In particular, the weight of the sample tray holder 266 is not received by the weighing device.

In FIG. 6 the inventive measuring instrument 210 of FIGS. 4 and 5 is shown in servicing position. To arrive at the servicing position, a portion of the movable housing part 222 has been swiveled about an essentially horizontal pivot axis 225 from the loading position into the servicing position. The sample-heating means 270 is arranged in the pivoting portion of the movable housing part 222 and is swiveled together with the pivoting portion of the movable housing part 222 during the change into the servicing position. As a result, the components in the movable housing part 222 are easily accessible for servicing. Arranged in the upper housing part 222 is the sample-heating means 270. During the measurement process, the sample-heating means 270 is protected by a glass shield 272. Surrounding the sample-heating means 270 is the upper part 274 of the interior draft shield.

To give a clearer view of the position and configuration of the sample-heating means 270, of the glass shield 272 and of the interior draft shield 274, the measuring instrument 220 is shown in FIG. 7 with the upper part 274 of the interior draft shield partially removed, and in FIG. 8 the movable housing part 222 is shown without glass shield 272.

Arranged on the cylinder end surface of the interior draft shield 274 is a reflecting surface which serves to reflect the heat radiation generated by the sample-heating means 270. The reflection can also be achieved with a suitable reflective material of the cylinder end surface or a reflective coating of the cylinder end surface. An essentially circular light-screening barrier 273 serves to concentrate the heat rays generated by the sample-heating means 270.

In servicing position, the sample-heating means 270 is oriented vertically. At least a part of the upper part 274 of the interior draft shield is attached to the movable housing part 222 by means of a plug-in connection, wherein the plug-in direction is essentially vertical in the servicing position. The glass shield 272 is clamped between the light-screening barrier 273 and a part of the upper part 274 of the interior draft shield 274. To remove the glass shield, only a part of the interior draft shield 274 needs to be pulled out of the plug-in connection. Subsequently, the glass shield can be removed simply by pulling it out, without using a tool. The easy removal of the glass shield 272 is of particular advantage, because it facilitates the taking-out and cleaning of the glass shield 272 which is prone to get dirty.

The glass shield 272 and/or a portion of the upper part 274 of the interior draft shield can be pulled out of the movable housing part in a controlled direction by means of a guide track 275. In the servicing position, the guide track 275 is oriented essentially vertical.

The removal of the glass shield 272 is additionally facilitated by a service opening 223. The service opening 223 is an access opening in the movable housing part 222 which is open only in the servicing position but not in the measuring position or in the loading position. An inadvertent touching of the sample-heating means is thereby prevented, which reduces the risk of burn injuries. The service opening is realized with a two-part configuration of the movable housing part. According to this concept, the two parts of the movable housing part are designed so that in the move to the servicing position a portion of the movable housing part does not participate in the swivel movement. This non-swiveled portion clears the access to the service opening in the swiveled portion of the movable housing part.

The width of the service opening 223 is advantageously equal to or larger than the width of the glass shield 272. This allows the glass shield to be removed easily. The service opening 223 is arranged at a right angle to the plug-in direction of the upper part of the interior draft shield 274 and in the extension of the path of the guide track 275. As a result of this arrangement, the glass shield 272 can easily be pulled out of the service opening 223.

The upper part of the interior draft shield 274 can be composed of several components. Advantageously, the portion that faces towards the service opening 223 can be removed without tolls. This requires he service opening 223 to be wider than the upper part of the interior draft shield 274.

The sample-heating means 270 can be attached to the movable housing part 222 in a variety of ways. For example, the sample-heating means 270 could be fastened to the movable housing part 222 by means of screws or with a plug-in connector. If a plug-in connector is used, the sample-heating means 270 can easily be pulled out for servicing. Ideally, this plug-in connection could be designed so that the plug insertion is directed essentially perpendicular to the plane of the service opening 223.

The sample-heating means 270, the light-screening barrier 273, the glass shield 272 and the upper part of the interior draft shield 274 have openings which, together with the outlet vent openings 227 allow the vapors and/or volatile substances escaping from a sample to be vented into the outside atmosphere. The openings are therefore arranged so as to ensure the direct venting of gases that escape from the sample. It is of advantage if these openings provide a direct line of vision to the sample that is located on the sample receiver 260, whereby a visual inspection of the measurement process is made possible.

In place of the interior draft shield 274 and the light-screening barrier 273, one could use other suitable attachment devices to hold the glass shield 272 in place.

Since the glass shield 272 is easy to take out, it can be cleaned more easily and quickly by the user or the service technician. Ideally, the glass shield 272 is made so that it can be cleaned in a conventional washing machine without damage.

The embodiments presented herein show, partially in schematic form, measuring instruments for the gravimetric determination of moisture content with different properties and features. For clarity's sake, the different properties and features have been presented in different sample illustrations, but it is also possible to realize some, several or all of the described features and properties in one and the same measuring instrument.

What is claimed is:

1. An instrument for gravimetrically determining moisture content of a sample, comprising:
   a housing, comprising:
      a stationary housing part; and
      a movable housing part, movable between a measuring position and a loading position; and
   a weighing device, arranged inside the housing and comprising:
      a load receiver, onto which the sample is placed when the movable housing part is in the loading position in which the stationary housing part and movable housing part are spaced apart from each other;
      a closed test compartment that surrounds the load receiver, formed by the stationary housing part and the movable housing part while in the measuring position; and
      a means for heating the sample placed on the load receiver, arranged on the movable housing part parallel to the load receiver; and
   a device that changes the position of the movable housing part both vertically and horizontally from the measuring position to the loading position by means of a movement in which the means for heating remains parallel to the load receiver in the loading position; and
   a means for selectively making and breaking an electrical contact, comprising:
      a first part, connected to the stationary housing part, through which electrical power from an electrical power source is connected; and
      a second part, connected to the movable housing part;
      the first and second parts arranged so that:
         in the measuring position, an electrical contact is made between the stationary housing part and the movable housing part, providing electrical power from the electrical power source to the means for heating the sample; and
         in the loading position, the electrical contact between the first and second parts is broken and no electrical power is provided from the electrical power source to the means for heating the sample.

2. The instrument of claim 1, wherein:
   the first part has a rigid connection to the stationary housing part; and
   the second part has a rigid connection to the movable housing part.

3. The instrument of claim 2, further comprising:
   an electronic contact means, arranged between the respective housing parts, through which a contact exists for transfer of control signals when in the measuring position and the contact is broken, preventing the transfer of control signals into the movable housing part when in the loading position.

4. The instrument of claim 3, further comprising:
   a displacement-guiding means for bringing the movable housing part in a translatory movement from the measuring position to the loading position such that the translatory movement breaks the electrical contact between the respective first and second parts of the electrical contact means.

5. The instrument of claim 4, wherein:
   the means for making and breaking electrical contact comprises a plug-in connection.

6. The instrument of claim 5, wherein:
   the plug-in connection comprises a plug and a corresponding socket, the plug being extracted from the socket in a vertical direction.

7. The instrument of claim 6, wherein:
   only the sample heating means is supplied with electricity through the electrical contact means.

8. The instrument of claim 3, wherein:
   the movable housing part moves simultaneously in the horizontal and vertical directions.

9. The instrument of claim 3, wherein:
   the movable housing part is located above the stationary housing part in both the measurement and the loading position.

10. The instrument of claim 1, wherein:
    the sample-heating means is arranged in the movable housing part so that:
    in the measuring position, the sample-heating means is located above the sample receiver; and
    in the loading position the sample-heating means is located above the stationary housing part.

11. The instrument of claim 1, wherein:
    the sample-heating means is arranged so that a surface thereof spreads horizontally over the sample receiver and between the stationary housing part and the movable housing part in at least one of the measuring position and the loading position.

12. The instrument of claim 1, wherein:
    the movable housing part has a portion, containing the heating means, which swivels about a horizontal pivot axis from the loading position into a servicing position, in which the heating means is accessible for servicing and is oriented in an essentially vertical position.

13. The instrument of claim 12, wherein:
    the movable housing part does not carry a voltage in either the loading position or in the servicing position.

14. The instrument of claim 1, wherein:
    the weighing device is arranged in the stationary housing part.

15. The instrument of claim 1, further comprising:
    an electronic contact means, arranged between the respective housing parts, through which a contact exists for transfer of control signals when in the measuring position and the contact is broken, preventing the transfer of control signals into the movable housing part when in the loading position.

16. The instrument of claim 1, wherein:
    the means for making and breaking electrical contact comprises a plug-in connection.

17. The instrument of claim 1, wherein:
only the sample heating means is supplied with electricity through the electrical contact means.

18. An instrument for gravimetrically determining moisture content of a sample, comprising:
- a housing, comprising:
  - a stationary housing part; and
  - a movable housing part, movable between a measuring position, in which the stationary and movable housing parts come together to define a test compartment that is closed, and a loading position, in which the stationary and movable housing parts are spaced apart from each other to open the test compartment;
- a weighing device, arranged inside the stationary housing part and comprising a load receiver, contained in the test compartment, for receiving the sample when the housing is in the loading position;
- a means for heating the sample, arranged on the movable housing part to face a top surface of the load receiver when in the measuring position;
- a guide that translates the movable housing part from the measuring position to the loading position in a motion that is both vertical and horizontal while maintaining the means for heating the sample parallel to the load receiver; and
- a means for selectively making and breaking an electrical contact, comprising:
  - a first part, connected to the stationary housing part, through which electrical power from an electrical power source is connected; and
  - a second part, connected to the movable housing part;
- wherein the first and second parts are arranged so that:
- in the measuring position, an electrical contact is made between the stationary housing part and the movable housing part, providing electrical power from the electrical power source to the means for heating the sample; and
- in the loading position, the electrical contact between the first and second parts is broken and no electrical power is provided from the electrical power source to the means for heating the sample.

\* \* \* \* \*